US00PP30536P3

(12) United States Plant Patent
Olesen

(10) Patent No.: US PP30,536 P3
(45) Date of Patent: May 28, 2019

(54) COMPACT FLORIBUNDS ROSE PLANT NAMED 'POULCAS054'

(50) Latin Name: ***Rosa* hybrid**
Varietal Denomination: Poulcas054

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 21 days.

(21) Appl. No.: 15/731,986

(22) Filed: Sep. 5, 2017

(65) Prior Publication Data

US 2019/0075701 P1 Mar. 7, 2019

(51) Int. Cl.
*A01H 5/02* (2018.01)

(52) U.S. Cl.
USPC ..... Plt./148
CPC ..... *A01H 5/02* (2013.01)

(58) Field of Classification Search
USPC ..... Plt./148
See application file for complete search history.

(56) References Cited

PUBLICATIONS

UPOV hit on floribunda rose plant named 'Poulcas054' QZ PBR 49229, filed Sep. 19, 2016.*

* cited by examiner

*Primary Examiner* — Anne Marie Grunberg

(57) ABSTRACT

A new garden rose plant of the Compact Floribunda class which has abundant, pink flowers and attractive foliage. This new and distinct variety has shown to be uniform and stable in the resulting generations from asexual propagation.

2 Drawing Sheets

Botanical designation: *Rosa* hybrid.
Variety denomination: 'Poulcas054'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2009 and the resulting seeds were planted in a controlled environment in Fredensborg, Denmark. The new variety, named 'Poulcas054', originated as a single seedling from the stated cross.

The new variety may be distinguished from its male pollen parent and female seed parent primarily by the following characteristics. The male pollen parent plant has a growth height of 100 cm while the newly claimed plant has a growth height of 50 cm. The female seed parent plant has Red-Purple Group N57C flowers while the new variety has Red-Purple Group 68B flowers.

The objective of the hybridization of this rose variety was to create a new and distinct variety with unique qualities, such as:

1. Uniform and abundant pink flowers;
2. Vigorous, but compact growth when propagated on its own roots;
3. Exceptional disease resistance; and
4. Perfumed flowers.

This combination of qualities is not present in previously available commercial cultivars of this type, known to the inventor, and distinguish 'Poulcas054' from all other varieties of which we are aware.

As part of the rose development program, Mogens N. Olesen germinated the seeds from the aforementioned hybridization during winter of 2009 and conducted evaluations on the resulting seedlings in a controlled environment in Fredensborg, Denmark. 'Poulcas054' was selected in the spring of 2010 by the inventor as a single plant from the progeny of the aforementioned hybridization.

Asexual reproduction of 'Poulcas054' by rooted cuttings was first done by Mogens N. Olesen in the nursery in Fredensborg, Denmark in July, 2010. This initial and other subsequent asexual propagations conducted in controlled environments have demonstrated that the characteristics of 'Poulcas054' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcas054'.

Specifically illustrated in FIG. 1 of the drawings are open flower, petals detached showing sepals and receptacle.

Figure 1:
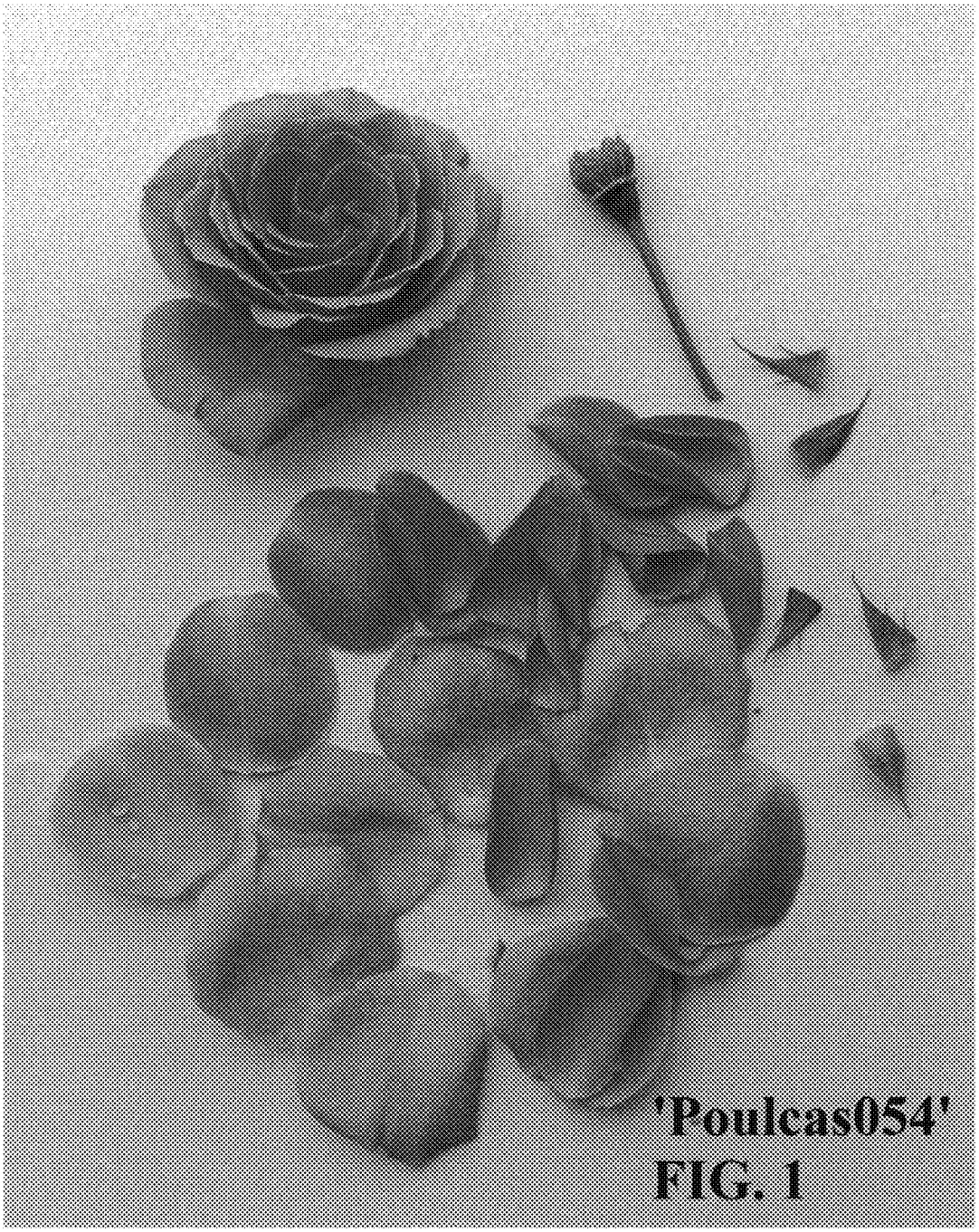
Figure 2:
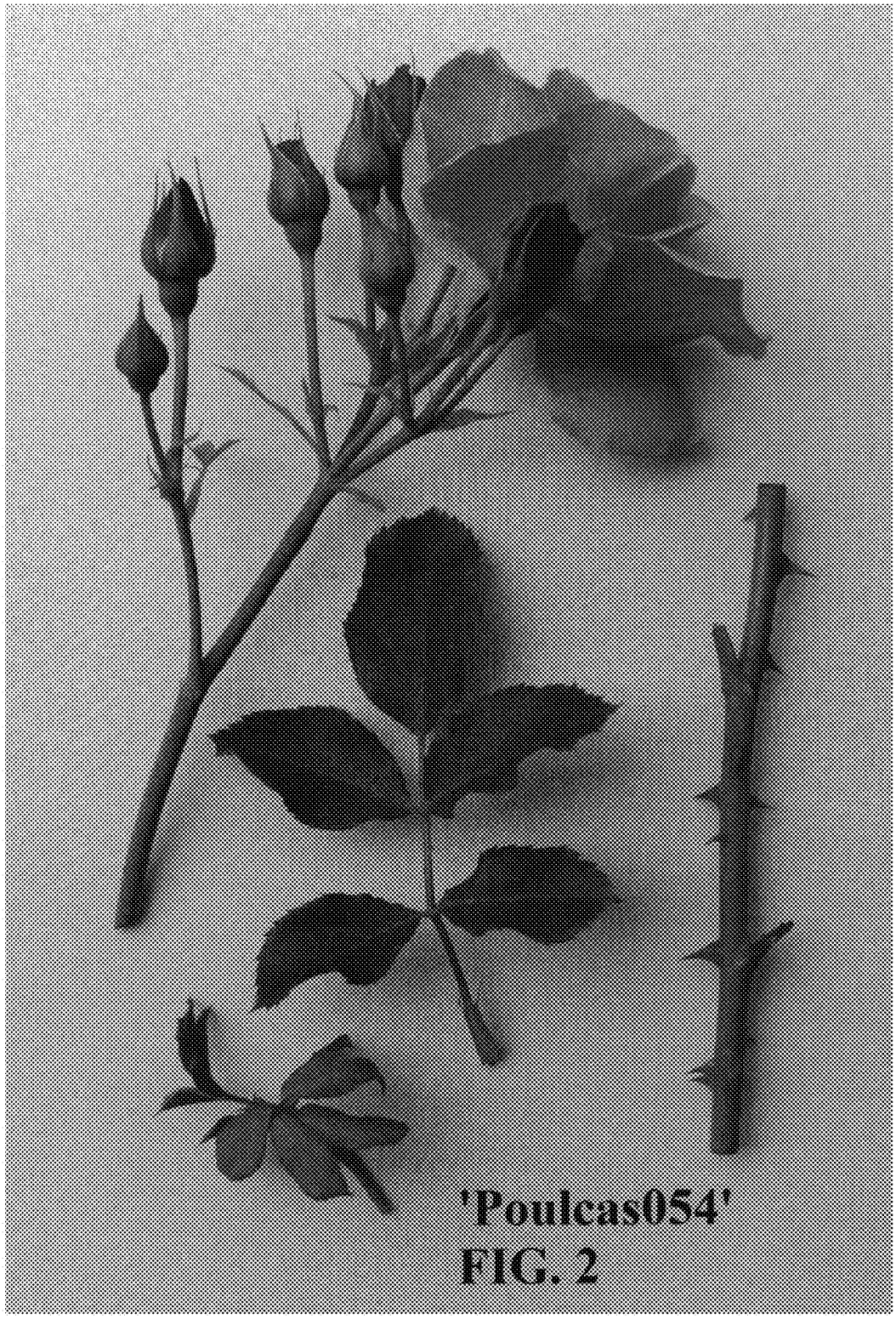

Specifically illustrated in FIG. 2 of the drawings are a cluster of flowers on a branch, leaves, and bare stem. Plants shown are 2 years of age.

DETAILED DESCRIPTION OF THE VARIETY

The following is a description of 'Poulcas054', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulcas031', U.S. Plant Pat. No. 22,502 are compared to 'Poulcas054' in Chart 1.

CHART 1

| | 'Poulcas054' | 'Poulcas031' |
|---|---|---|
| Petal Count | 30 petals | 40 to 50 petals |
| Flower Diameter | 95 mm | 70 to 80 mm |
| General Tonality of Flower Color | Red-Purple Group 68B | Red-Purple Group N57A |

Flower and flower bud:

*Blooming habit*.—Continuous.

*Flower bud*.—Size: Upon opening, 27 mm in length from base of receptacle to end of bud. Bud diameter is 12 mm. Bud form: Ovoid. Bud color: As sepals divide petals are Red Group 47A with intonations of Red Group 53A. Sepal inner surface: Color: Yellow-Green Group 144B. Surface: Lightly pubescent. Sepal outer surface: Color: Yellow-Green Group 144A. Texture: Smooth. Sepal Shape: Apex: Cirrhose. Base: Flat at union with receptacle. Sepal Margin: Margins have weak foliaceous appendages on three of the five sepals. Sepal size: 28 mm long, 10 mm wide. Receptacle: Texture: Smooth. Size: 7 mm in height, 7 mm wide. Color: Yellow-Green Group 144A. Shape: Campanulate. Pedicel: Surface: Smooth. Length: 30 mm. Diameter: 3 mm on average. Color: Yellow-Green Group 151A with intonations of Greyed-Red Group 180D. Strength: Strong. Peduncle: Length: 3 cm average. Diameter: About 4 mm. Color: Yellow-Green Group 146C. Texture: Smooth.

*Flower bud development*.—Flower buds are borne in clusters of about 5 to 9 flower buds per stem.

*Flower bloom*.—Fragrance: Strong perfume. Duration: The blooms have a duration on the plant of approximately 10 days. Petals fall cleanly away from plant after flowers have fully matured. Size: Flower diameter is 95 mm when open. Flower depth is 35 mm. Flower shape: High centered, double, with a high pointed center which is tightly closed.

*Petalage*.—Under normal conditions, flowers have about 30 petals.

*General tonality of flower*.—Open flowers are Red-Purple Group 68B.

*Petal color*.—Upon opening and after opening, outer petals Upper surface: Red-Purple Group 68B with marginal intonations of Yellow-Green Group 8D. Lower surface: Red-Purple Group 58D with streaks of Yellow Group 8D. Upon opening and after opening, inner petals: Upper surface: Red Group 55A. Lower surface: Red Group 52C. Basal petal spots, upon opening and after opening: Upper surface: Yellow Group 9D. Lower surface: Yellow Group 8C.

*Petals*.—Petal Reflex: Somewhat reflexed. Margin: Entire and uniform. Moderate undulations. Shape: Broad and elliptic. Apex shape: Rounded. Base shape: Acute. Size: 50 mm (l)×50 mm (w). Texture: Smooth. Thickness: Average.

*Petaloids*.—None observed.

*Reproductive flower parts*.—Pollen: None observed. Anthers: Size: 3 mm in length. Color: Yellow-Orange Group 16A. Quantity: 35 on average. Filaments: Color: Yellow Group 13A and Orange-Red Group 31B. Length: 7 mm. Pistils: Length: 6 mm. Quantity: 20 on average. Stigmas: Color: Greyed-Yellow Group 160D. Styles: Color: Yellow-Green Group 154D. Location of stigmas: Inferior in location relative to the length of the filaments and the height of the anthers. Hips: None Observed.

Plant:

*Plant growth*.—Upright, bushy. Plants are 50 cm in height, and 45 cm wide.

*Stems*.—Color of juvenile growth: Yellow-Green Group 144A. Color of mature growth: Yellow-Green Group 144B. Length: Canes are about 25 cm from the base of the plant to the flowering portion. Diameter: About 7 mm. Internodes: On mature canes about 40 mm between nodes. Surface Texture: Young wood: Smooth. Older wood: Smooth.

*Long prickles*.—Incidence: 10 prickles per 10 cm of stem. Size: Average length of prickles on mature stems is 5 mm. Shape: Upper portion is linear. Lower portion is concave. Color: Juvenile prickles: Greyed-Red Group 180A. Mature prickles: Greyed-Red Group 180A and Greyed-Orange Group 165C.

*Plant foliage*.—Compound leaf: 135 mm (l)×95 (w). Quantity: 2 leaves per 10 cm of stem on average. Leaf bearing angle to the stem: 45 degrees. Color of juvenile foliage: Upper side: Yellow-Green Group N144A with intonations of Greyed-Purple Group 183B. Lower side: Yellow-Green Group 146D. Color of mature foliage: Upper side: Yellow-Green Group 146A. Lower side: Yellow-Green Group 147C.

*Plant leaves and leaflets*.—Stipules: Size: 25 mm long, 2 mm wide. Quantity: 2 per compound leaf. Shape: Linear, slightly broad based with outward extending apices. Margins: Finely serrated. Color: Yellow-Green Group 144B. Petiole: Length: 40 mm. Diameter: 2 mm. Upper surface color: Yellow-Green Group 144B. Lower surface color: Yellow-Green Group 144B. Rachis: Length: 40 mm. Diameter: 2 mm. Upper surface color: Yellow-Green Group 144B. Lower surface color: Yellow-Green Group 144B. Leaflet: Quantity: Normally 5 leaflets. Margins: Serrated. Size: Terminal leaflets are about 46 mm long, 35 mm wide. Shape: Generally elliptical. Base: Rounded. Apex: Cuspidate. Texture: Smooth. Thickness: Above average. Arrangement: Odd pinnate. Venation: Reticulate. Glossiness: Weak.

*Disease resistance*.—Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

*Cold hardiness*.—The variety is tolerant to USDA Cold Hardiness Zone 6.

*Heat tolerance*.—The variety has been found to be suitable for climate conditions found in the American Horticulture Society heat zone 7.

We claim:

1. A new and distinct variety of rose plant of the Compact Floribunda rose class named 'Poulcas054', substantially as illustrated and described herein, due to its abundant pink flowers, disease resistance, and extended period of bloom.

* * * * *

'Poulcas054'

'Poulcas054'